United States Patent [19]

Taniguti

[11] Patent Number: 4,614,117
[45] Date of Patent: Sep. 30, 1986

[54] VIBRATION MONITORING APPARATUS

[75] Inventor: Ryousuke Taniguti, Nagasaki, Japan

[73] Assignee: Mitsubishi Denki Kabushiki Kaisha, Tokyo, Japan

[21] Appl. No.: 702,504

[22] PCT Filed: Jul. 11, 1984

[86] PCT No.: PCT/JP84/00354
§ 371 Date: Feb. 7, 1985
§ 102(e) Date: Feb. 7, 1985

[30] Foreign Application Priority Data

Jul. 11, 1983 [JP] Japan .................. 58-127464

[51] Int. Cl.⁴ ............................. G01N 29/04
[52] U.S. Cl. ........................... 73/659; 73/660; 340/683; 364/508
[58] Field of Search ............... 73/659, 660; 364/508; 340/683

[56] References Cited

U.S. PATENT DOCUMENTS

| | | | |
|---|---|---|---|
| 4,426,641 | 1/1984 | Kurihara et al. | 73/660 |
| 4,435,770 | 3/1984 | Shiohata et al. | 73/660 |
| 4,437,163 | 3/1984 | Kurihara et al. | 364/508 |
| 4,520,674 | 6/1985 | Canada et al. | 73/660 |

FOREIGN PATENT DOCUMENTS 58-50433  3/1983  Japan .
58-50435  3/1983  Japan .

*Primary Examiner*—Howard A. Birmiel
*Attorney, Agent, or Firm*—Leydig, Voit & Mayer, Ltd

[57] ABSTRACT

An apparatus monitoring the vibrations of a rotary machine precisely at all times. In a control processor, a rotational frequency is calculated with a data signal from a register which operates on the basis of period pulses from a key phaser, while a vibration lever corresponding to the rotational frequency is read out of a memory, and an alarm level obtained by giving the vibration level a constant from an alarm level setting unit is sent to a signal processor. The vibration waveform of a vibration sensor selected by a scanner is converted by an A/D converter into a digital signal, which is applied to the signal processor through a shift register. In the signal processor, the alarm level from the control processor is compared with vibration data from the shift register, and the calculated result is sent to the control processor. The control processor operates output appliances on the basis of the information from the signal processor.

6 Claims, 4 Drawing Figures

VIBRATION MONITORING APPARATUS

TECHNICAL FIELD

This invention relates to a vibration monitoring apparatus which is furnished with a plurality of vibration detectors in the rotational system of a rotary machine such as a turbogenerator or a large-sized variable-speed rotary machine and which has the function of sounding an alarm or energizing a stopping relay for the rotary machine when any abnormal vibration has occurred.

BACKGROUND ART

Heretofore, vibration monitoring apparatus of this type is known which is so constructed that a vibration level detected by a vibration detector mounted on a rotary machine or the like is compared with an alarm level for a fixed period according to the rotational frequency of the rotary machine, so that when the vibration level reaches the alarm level, the single-sided amplitude value of the vibration waveform is calculated by a computer, and that when the calculated result exceeds a control criterion, an alarm is provided.

In vibration monitoring apparatus of this type, it is an important factor that the processing of vibration signals detected by a plurality of vibration detectors is performed at high precision and at high speed by a computer system.

DISCLOSURE OF THE INVENTION

This invention provides a vibration monitoring apparatus having a key phaser for detecting the period of rotation of a rotary member to-be-monitored and vibration sensors and a vibration waveform in the information time interval of one period of the rotary member is subjected to digital signal processing by a control processor and a signal processor. The amplitude value of the vibration waveform is calculated and compared with a control value for the rotational frequency of the rotary member, the apparatus being capable of calculating a vibration level precisely and processing signals at high speed.

According to this invention, a memory is provided for storing a rotational frequency - versus - vibration level pattern whereby an alarm can be appropriately set at the speed change of the rotary member, and a vibratory abnormality can be found early.

BEST MODE FOR CARRYING OUT THE INVENTION

Figure 1:
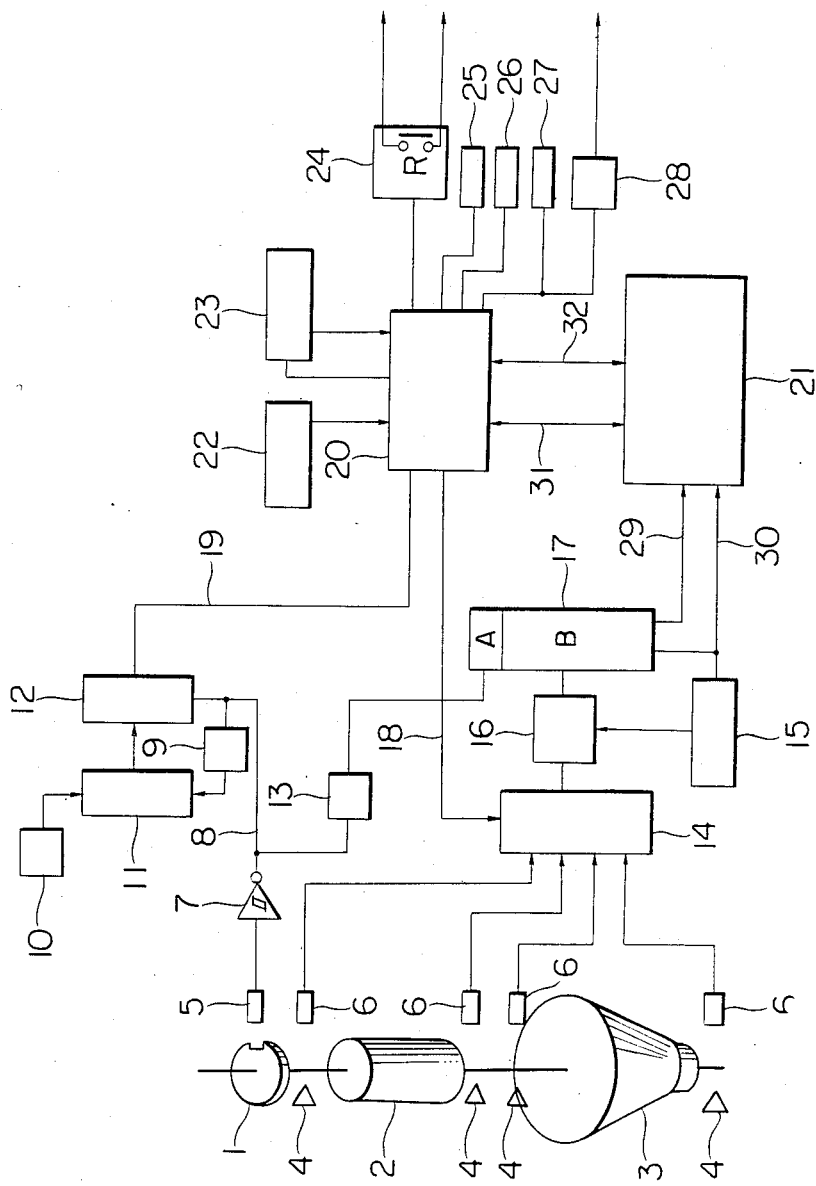
FIG. 1 is a block diagram showing the arrangement of a vibration monitoring system according to an embodiment of this invention.

Now, one embodiment of this invention will be described with reference to the drawings. In FIG. 1, (1) designates a rotation mark which is directly coupled to the shaft of the rotor (2) of, for example, a turbogenerator being a rotary machine to-be-monitored, (3) a turbine, (4) bearing stands which bear the rotary shaft of the turbogenerator, (5) a key phaser which is arranged in opposition to the rotation mark (1) and which detects the rotation of the rotation mark (1) to detect the period of rotation of the rotary machine, and (6) vibration sensors which are fixed to the housing of the rotary machine and which are usually composed of X-axis sensors and Y-axis sensors situated in positions in directions orthogonal to the axis of the rotary shaft and in directions orthogonal to each other. (7) denotes a waveshaping unit, (9) a delay monostable multivibrator, (10) a clock generator for a period counter, (11) the period counter, (12) a register, (13) a binary counter, (14) a scanner, (15) a clock generator for A/D (analog/digital) conversion control, (16) an A/D converter, (17) a shift register, (20) a control processor, (21) a signal processor, (22) an alarm level setting unit, (23) a rewritable nondestructive memory in which a pattern of rotational frequencies - versus - vibration levels is stored, (24) an alarm relay, (25) a rotational frequency indicator, (26) a scanner channel indicator, (27) a vibration level indicator, and (28) a D/A (digital/analog) converter.

In addition, (8) denotes a period pulse (a latch signal for the register), (18) a channel set signal, (19) a data signal from the register (12), (29) a serial data signal from the shift register (17), (30) a shift clock, (31) transfer data, and (32) a control signal.

The control processor (20) and memory (23) constitute a main processor unit; the waveshaping unit (7), delay monostable multivibrator (9), clock generator (10), period counter (11) and register (12) constitute a speed relay unit; the binary counter (13), scanner (14), clock generator (15), A/D converter (16), shift register (17) and signal processor (21) constitute a signal processor unit; and the alarm relay (24), rotational frequency indicator (25), scanner channel indicator (26), vibration level indicator (27) and D/A converter (28) constitute an output unit.

Next, the operation will be explained. The signal of the key phaser (5) which is delivered, for example, each time the rotation mark (1) rotates is waveshaped by the waveshaping unit (7), and the data of the period counter (11) is latched into the register (12) by the rise of the synchronizing pulse. The period pulse (8) from the waveshaping unit (7) is also applied to the synchronizing counter (11) through the delay monostable multivibrator (9), to reset the counter (11) a fixed time (a short time) after the latch has been completed. Accordingly, each time the rotor (2) executes one revolution, one item of data is stored in the register (12). This data is updated periodically. The control processor (20) reads the data signal (19) from the register (12), and calculates the revolution number of every minute by an internal operation. Data indicative of the revolution number calculated by the control processor (20) is delivered to the rotational frequency indicator (25). Besides, in the control processor (20), a normal vibration level at the actual rotational frequency obtained by the calculation is read from the memory (23) in which the pattern of rotational frequencies - versus - vibration levels is stored in advance, and an alarm level which is a value obtained by multiplying the normal vibration level by a constant received from the alarm level setting unit (22) is sent to and set in the signal processor (21), while the first channel of the scanner (14) is set. Then, a vibration waveform from the vibration sensor (6) is applied to the A/D converter (16). The A/D converter (16) is controlled by the clock generator (15) which can sample the vibration waveform sufficiently finely, and digitized vibration data is applied to the portion B of the shift register. Further, the period pulses (rotational frequency pulses) from the waveshaping unit (7) have their frequency divided once by the binary counter (13), and the resulting information is applied to the portion A of the register (17). The information is transferred to the signal processor (21) at each A/D conversion operation. The signal processor (21) accepts the vibration data only during the information time interval in which the data of the portion A of the register is either "1" or "0" (the period of time of one revolution), so as to calculate the value of a single-sided amplitude or double-sided amplitude in accordance with a predetermined program.

Figure 2:
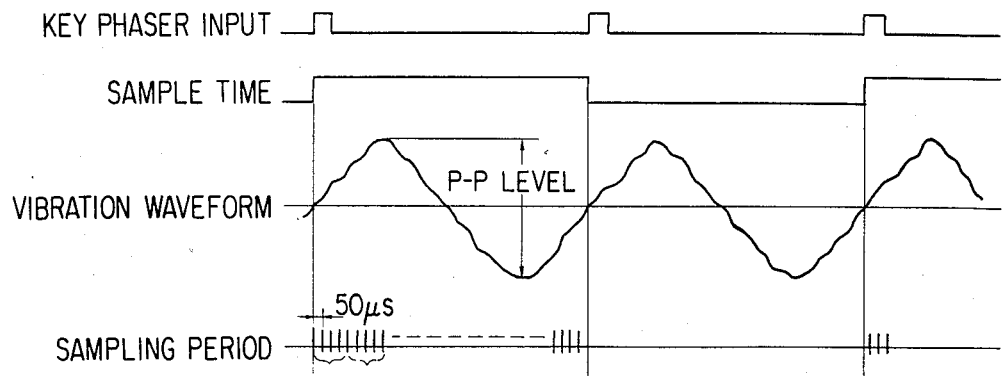
FIG. 2 is a signal waveform diagram showing several signals for calculating the amplitude value of a vibration waveform in the system of FIG. 1.
Figure 3:
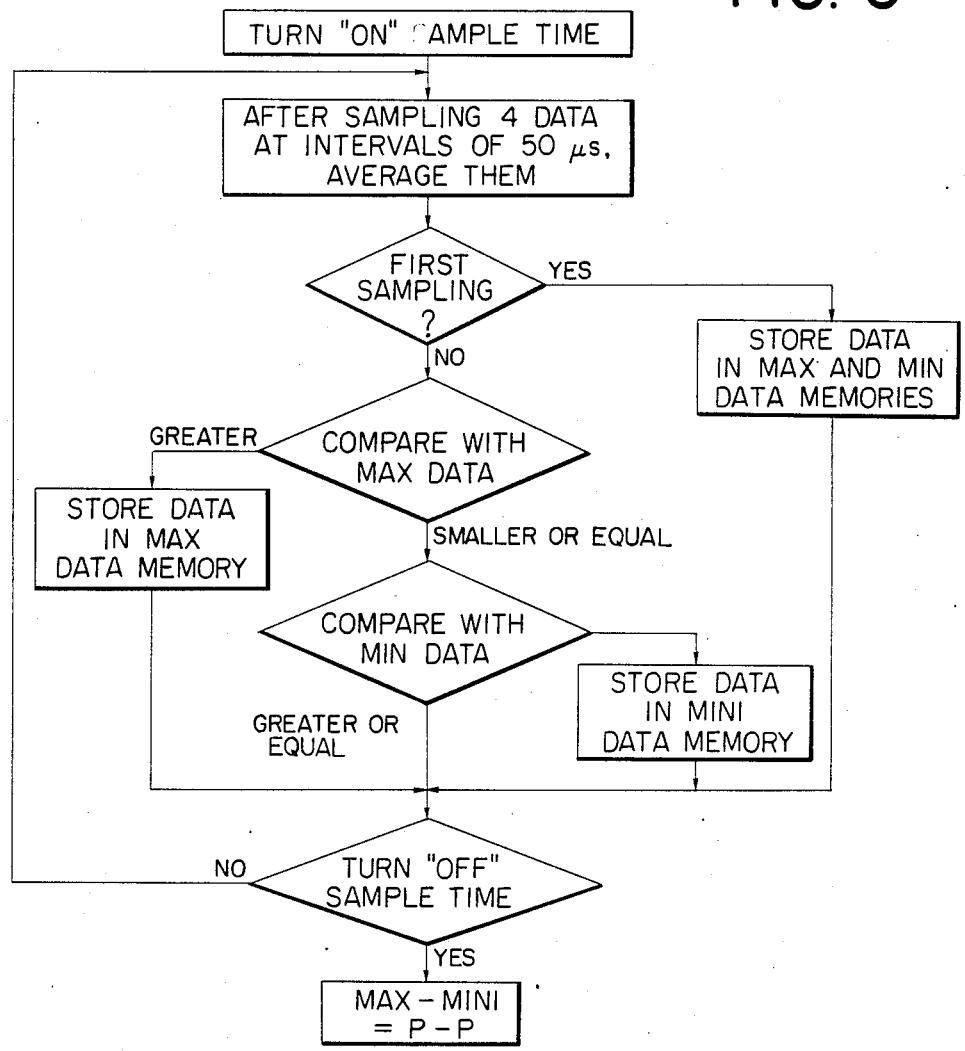
FIG. 3 is a flow chart showing an algorithm for calculating the double-sided amplitude value of the vibration waveform in the system of FIG. 1.

FIGS. 2 and 3 show signals indicative of a key phaser input, a sample time, a vibration waveform and a sampling period, and a calculating algorithm in the case of finding the both-sided amplitude value of the vibration waveform. Here, the sample time is determined by an operation from the key phaser input or the number of poles. As calculated data, the mean value of four items of sampling data is employed. Further, the first sampled data is stored in MAX (maximum) and MIN (minimum) data memories in the first operation of the double-sided amplitude (peak-to-peak level), whereby P-P magnitude can be rendered zero in case of a D.C. input.

Further, in the signal processor (21), the data of the vibration level thus calculated is compared with the preset alarm level. The signal processor judges the rotary machine to be abnormal when the above data is greater than the alarm level, and to be normal when the former is smaller than the latter. It supplies the control processor (20) with a calculation end signal in parallel with the vibration level beforehand, and thereafter delivers the data thereto.

Upon receiving the information, the control processor (20) indicates the vibration level by means of the vibration level indicator (27), and it energizes the alarm relay (24) in the case of the abnormality. The channel of the scanner (14) at that time is indicated by the scanner channel indicator (26). When the vibration level is externally sent as analog information, the D/A converter (28) is driven.

When the first channel has ended, the same operations are repeated for the second channel et seq. The channels of the scanner (14) are correspondingly provided by the number of the vibration sensors (6). When the operations have ended for all the channels, rotational frequency information is read out again. Thenceforth, the same operations are repeated.

Figure 4:
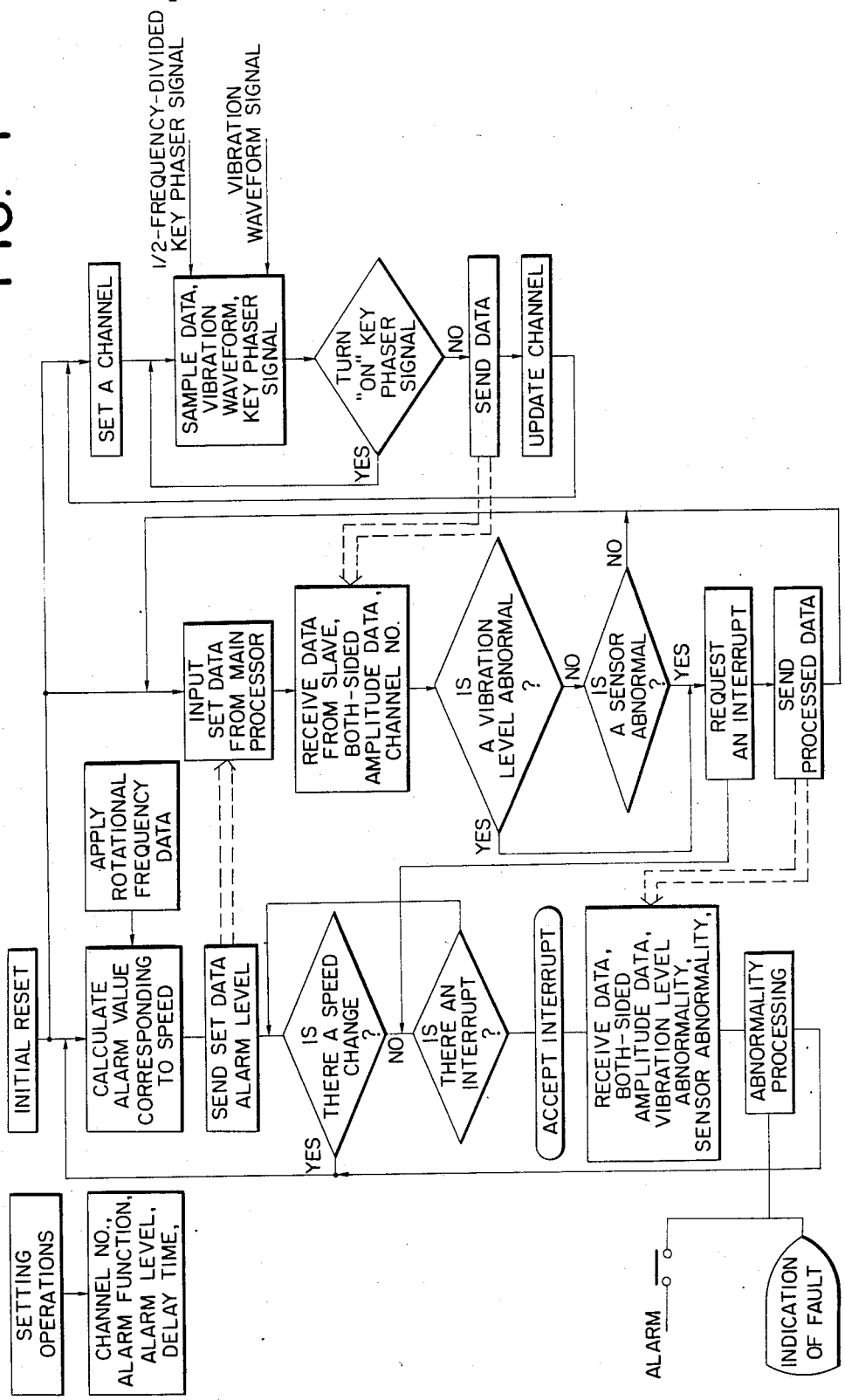
FIG. 4 is a general flow chart showing the operation of a vibration monitoring apparatus according to this invention.

FIG. 4 shows a general flow chart in the case of executing the alarm processing of the vibration monitoring apparatus in this invention.

In this manner, the control processor and the signal processor are conjointly used, and the control processor performs the automatic level setting of an alarm, the acknowledgement of an alarm signal, the selection of the output scanner of the alarm signal, the outputing of a vibration level, and the calculation and outputing of a rotational frequency, while the signal processor performs the momentary calculation of a vibration waveform during one period, the decision of a vibration level calculation alarm, and the decision of the abnormality of the sensors, whereby a vibration monitoring system which ensures a diagnosis of high speed and high precision can be provided.

While, in the above embodiment, the rotational frequency/vibration level pattern and the alarm have been set so as to be common to the respective axes (sensors), such patterns and alarms can also be set individually for the respective sensors. Besides, the output indicators may well be replaced with a CRT display. Further, the rotational frequency can also be calculated by the signal processor.

As set forth above, according to this invention, in monitoring the vibrations of a plurality of places in an identical rotational system, the digital signal processing of an instantaneous waveform is permitted by disposing a rotational pulse detector, a vibration sensor selecting scanner and an A/D converter and by employing both a control processor and a signal processor, whereby the precision of a vibration calculation is enhanced, and the raised speed of a diagnosis can be expected, so that the reliability is extraordinarily enhanced.

By introducing a memory which stores a rotational frequency/vibration level pattern, it has been permitted to set an appropriate alarm at the time of a speed change and to find a vibrational abnormality at an early stage.

INDUSTRIAL APPLICABILITY

This invention is applicable to an apparatus which normally monitors the vibrations of a large-sized rotary machine such as a turbogenerator.

What is claimed is:

1. A vibration monitoring apparatus comprising a key phaser for detecting rotation of a rotary member, a period counter for receiving an output of said key phaser, a register for latching data of said period counter, an alarm level setting unit, a memory for storing a rotational frequency/vibration level pattern, a plurality of vibration sensors for detecting vibrations of said rotary member, a vibration sensor selecting scanner for receiving outputs of the respective vibration sensors, a control processor including means for generating an alarm level at a predetermined rotational frequency on the basis of outputs from said register, said alarm level setting unit and said memory, an A/D converter for converting into a digital signal a vibration waveform output from the vibration sensor selected by said vibration sensor selecting scanner, a vibration waveform data input register for receiving an output of said A/D converter, a signal processor including means for comparing an output of said vibration waveform data input register and the alarm level from said control processor, for calculating the result of the comparison, and for sending a calculated result to said control processor, and output appliances for receiving and operating responsive to an output from said control processor based on said calculated result of said signal processor.

2. A vibration monitoring apparatus as defined in claim 1 wherein said control processor and said signal processor are conjointly used, said control processor includes means for setting an automatic level of an alarm, acknowledging an alarm signal, selecting an output scanner for the alarm signal, outputting a vibration level, and calculating and outputting a rotational frequency, and said signal processor includes means for calculating a vibration waveform during one period to determine a vibration level and deciding whether an abnormality exists in the sensors so as to cause an alarm.

3. A vibration monitoring apparatus as defined in claim 2 wherein the calculation of the rotational frequency is processed by said signal processor.

4. A vibration monitoring apparatus as defined in claim 1 or claim 2 wherein a single alarm setting level and a single rotational frequency/vibration level pattern are provided so as to be common to respective channels.

5. A vibration monitoring apparatus as defined in claim 1 or claim 2 wherein alarm setting levels and rotational frequency/vibration level patterns are provided individually for respective channels.

6. A vibration monitoring apparatus as defined in claim 1 wherein said output appliances include a rotational frequency indicator, an alarm relay, a channel indicator, a vibration level indicator and a vibration level analog output unit.

* * * * *